United States Patent
Chen et al.

(10) Patent No.: US 12,157,917 B2
(45) Date of Patent: Dec. 3, 2024

(54) SPECIFIC DNA FRAGMENT OF FEMALE ACIPENSER DABRYANUS AND METHOD FOR IDENTIFYING THE SEX OF ACIPENSER DABRYANUS

(71) Applicant: CHINESE STURGEON RESEARCH INSTITUTE OF CTG, Yichang (CN)

(72) Inventors: Lei Chen, Yichang (CN); Zhiyuan Li, Yichang (CN); Yuanjin Yang, Yichang (CN); Yacheng Hu, Yichang (CN); Xin Zhu, Yichang (CN); Hejun Du, Yichang (CN); Dezhi Zhang, Yichang (CN)

(73) Assignee: CHINESE STURGEON RESEARCH INSTITUTE OF CTG, Yichang (CN)

( * ) Notice: Subject to any disclaimer, the term of this patent is extended or adjusted under 35 U.S.C. 154(b) by 0 days.

(21) Appl. No.: 18/173,060

(22) Filed: Feb. 23, 2023

(65) Prior Publication Data

US 2024/0117430 A1   Apr. 11, 2024

(30) Foreign Application Priority Data

Oct. 9, 2022 (CN) .......................... 202211228080.7

(51) Int. Cl.
*C12Q 1/6879* (2018.01)
*C12Q 1/686* (2018.01)

(52) U.S. Cl.
CPC ........... *C12Q 1/6879* (2013.01); *C12Q 1/686* (2013.01)

(58) Field of Classification Search
CPC ............................... C12Q 1/6879; C12Q 1/686
See application file for complete search history.

(56) References Cited

U.S. PATENT DOCUMENTS

2013/0244261 A1   9/2013   Wetzel et al.

FOREIGN PATENT DOCUMENTS

| CN | 111471775 A | 7/2020 |
|---|---|---|
| CN | 112680533 A | 4/2021 |

OTHER PUBLICATIONS

Chen, Y. et al., Gonadal transcriptome sequencing of the critically endangered Acipenser dabryanus to discover candidate sex-related genes, PeerJ, vol. 6, e5389, pp. 1-24 (Year: 2018).*
First Notification of Office Action by CNIPA, dated May 26, 2023, whole translation.
Notification to Grant Patent Right for Invention by CNIPA, dated Jun. 27, 2023, whole translation.
"A Study on the Complete Sequence of Mitochondrial DNA and Molecular Evolution of Sturgeniformes in Chinese Sturgeons and Acipenser Darkii", Wang Denggiang, D052-10, Issue 3, China Excellent Doctoral and Master's Thesis Database (Master's), Agricultural Science and Technology Journal, Mar. 15, 2006.
Liu Xueqing; Lisa, Xiao, Zhao; Guo Bofu; Chen Lei, Du Hejun; Screening of Sex-specific Markers in Acipenser sinensis Using AFLP, Sichuan Animal, 05, Aug. 17, 2015, pp. 714-718.
Yeyu Chen et al, Gonadal transcriptome sequencing of the critically endangered Acipenser dabryanus to discover candidate sex-related genes, PeerJ, vol. 6, Jul. 27, 2018, pp. 1-24.

\* cited by examiner

*Primary Examiner* — Samuel C Woolwine
(74) *Attorney, Agent, or Firm* — JCIPRNET

(57) ABSTRACT

A genome-specific gene sequence fragment of female *Acipenser dabryanus* and a method for identifying the sex of *Acipenser dabryanus* are disclosed. The gene sequence fragment of *Acipenser dabryanus* is used to identify the sex of *Acipenser dabryanus*. The method includes: performing PCR amplification on the DNA of the *Acipenser dabryanus* to be tested, and judging that the *Acipenser dabryanus* to be tested is female when a resultant product from the amplification shows 3 bands on an agarose gel and the *Acipenser dabryanus* to be tested is male when a resultant product from the amplification shows 2 bands on an agarose gel, alternatively, judging that the *Acipenser dabryanus* to be tested is female when a resultant fragment from the amplification has a 1402 bp band and it is male if there is no 1402 bp band. The gene sequence fragment is used to quickly and efficiently identify the sex of *Acipenser dabryanus*.

3 Claims, 1 Drawing Sheet

Specification includes a Sequence Listing.

SPECIFIC DNA FRAGMENT OF FEMALE ACIPENSER DABRYANUS AND METHOD FOR IDENTIFYING THE SEX OF ACIPENSER DABRYANUS

INCORPORATION-BY-REFERENCE OF MATERIAL SUBMITTED AS AN XML FILE VIA THE PATENT ELECTRONIC SYSTEM

This application contains Sequence Listing XML file as a separate part of the disclosure, the name of the XML file is "SX202301_SEQUENCE_LISTING", the date of creation of the XML file is Feb. 22, 2023, and its size is 8000 bytes. The entire contents of the XML file are hereby incorporated by reference.

FIELD

The present invention relates to a specific DNA fragment of female *Acipenser dabryanus* and a method for identifying the sex of *Acipenser dabryanus*, pertaining to the technical field of molecular genetics of animals.

BACKGROUND

The Yangtze sturgeon, also known as *Acipenser dabryanus*, is a unique species in the upper reaches of the Yangtze River in China, and of great scientific value in studying the earth's climate change and fish evolution. In recent years, due to overfishing, environmental pollution and other reasons, the Yangtze sturgeons have drastically slumped, and they have become a critical (CR) species and are facing extinction.

Most vertebrates are dioecious, and have distinct sexual dimorphism in morphology and physiology. Sex is a basis for determining the reproductive reproduction between both sexes. With the development of molecular biology, many types of sex markers have been developed, involving microsatellite markers, single nucleotide polymorphism, randomly amplified polymorphic DNA, and restriction fragment length polymorphism. Developing and applying sex-specific molecular markers and identifying sex-determining genes, on the one hand, enable sex-related economic traits to improve, and provide necessary tools for realizing sex-controllable breeding, on the other hand, they also lay foundation for the molecular mechanism of fish sex determination to be elucidated. Sex markers are an important tool for the development of sex-controllable technology.

At present, sex markers developed for all species of fish can only be linked to a single male fish or a single female fish. The sex markers that are only linked to a single sex have a common drawback. For example, the sex-linked gene mark for a species of fish is linked to a single female one of this species, so in the case that a target gene fragment cannot be amplified in a single male fish, providing no experimental error during the experimental manipulation, for instance, no failure in amplifying the target fragment from the experimental results caused by unsuccessful extraction of DNA, drug omission or error caused, experimenters will mistakenly think that the test sample is male, but the experiment is essentially unsuccessful. In order to avoid this occurrence, it is necessary to develop a special sex marker that amplifies the corresponding DNA fragments in both a single male fish and a single female fish. However, the results of amplification on the single male and female are not identical, for instance, both differ from each other in the size and number of amplified DNA fragments. The present invention provides a special sex mark for the forementioned *Acipenser dabryanus*.

SUMMARY

An objective of the present invention is to provide a genome-specific gene sequence fragment of female *Acipenser dabryanus* and a method for identifying the sex of *Acipenser dabryanus*.

A genome-specific gene sequence fragment of female *Acipenser dabryanus* has the nucleotide sequence of SEQ ID NO:1.

A positive reference DNA fragment amplified from both male and female *Acipenser dabryanus* has the nucleotide sequence of SEQ ID NO:2.

The nucleotide sequence of SEQ ID NO:1 and the nucleotide sequence of SEQ ID NO:2 are applied to identify the sex of *Acipenser dabryanus*.

The specific molecular marker is represented by the nucleotide sequence of SEQ ID NO:1. The nucleotide sequence of SEQ ID NO:1 serves as a genome-specific fragment of female *Acipenser dabryanus*, of which the primer is R6R2. The nucleotide sequence of SEQ ID NO:1 is:

AGGGAGATTGTTGACTAGGATTCATTCGCTCTCTGTCACAGTCCCGCATA
TGTGATCAAGGTTCGTAGAACAGCTTTTACTTCTGCCCCTTTGTGCTGAA
TAATTTGGTGGACATTGATGTAGTGAGTCCATTTCCTGGGAATGAATAGC
AAACCCAGTGTGTTATTGGCCCTTGTCCCAATAGTGTGATCATCAATAT
ACACTGATGTGGCAGTGACATCGGGTGTGGTTGTAAAGGGAGACGGCAGA
TGTGTTTGTGGGGGGGTGCAGTCATGTGGGGTACCGGTGTATAGCAGGG
CTGTGGGAAGCATGGCAACTGGTATGTGTTTACATGACAGGTTTCGTTCT
GATAAAGACAGGGTCCACCCGGCCAATCGAGCGTTGGATATGCCCTTAAC
GCTGCCATTGAGCAAAAGTTGGATAGGAGTGTGTTCTGTTTGCACTGTAA
TGTGTTGAAAACCTGTAATAAATTTGAAATATAGAACAGCCCAATATACA
GATAGCAGGTGACGAGTACACTGATCAAAAGCTTGCTCAACGGCTTTGAG
TAGCCTTGAAGCGTAGGCGACGGGATGTAGCTTGGTATTTACTTCCTGTA
ACAAAACTGCAGAGAGAAGTTTTGGTAGCTGCAGTCTGCAAAATAAGGGG
TTCATTAGAAGCCAGATTTCGGAGGGCATGTGCTTCTAGCAGGGAGGCTT
TGAGAGATTCAAAAGCAGTCTAATGTTTGCTTTCCCATACCAACACATCC
TTGCCTTTCCTGGAACCTTTCAACAGATCATAAAGTGGTTTAGCCTTGGA
TGAAAAGTCCTCAAACTCACAACAAAAATTGACCAGACCTAGAAAGGAAC
GTAAAGCAGTTTTCAGAGGTTGGCACAGGCAGCCACTGTACAGTTTCCAC
TTTGTGTTTGTCTGGGGACCGTCCTCCTTCCTCAATGAGTACCCCTAGAA
AAGTAACAGAAGGTTGCATTAGTTGTGCTTTTTTGGGTTCAGATTGAGTC
CTGCATTCTCTGTTGTTGTCAACAGCTCATCCAGCAGTGAGAGATGCTCC
TCCTTTGAGTGTCTGTCAGTAAGTCATCGACATAATGTATTAAACATTGG
GGTTTAGAGAAGCAGGACAAAATTTCAGAAAGTATTTGGTGAAAGAGCGT
GGGAGAGTTGTGGAACCCTTGCGGAATTTTATTCCAGGTATACTGTGTAT

-continued
```
CGCCAAAAGTGAAACCAAATTTATAGCGTGATTCTGGTTTCACTGGCAGA

GACCAGAAACCATTAAAAATGTCAAGAGCGGTGTAATAGCAGGCAGAAGG

GGTTAACTCAGAAAGCACATTTGGGGTAGATGCGTCTACAGGTGCGCATA

TAGGTGTGTGTTTAAGTTCCATGTAATCAATTGTAAGTCGCCAAGAACCG

TC.
```

The primer of the positive reference DNA fragment amplified from both male and female *Acipenser dabryanus* (SEQ ID NO:2) is R4R3, and this DNA fragment is:

```
TTGGAGAAGCCTACTGGGAAAGACGCAGAAATTTTAATTTCCCAAATGTT

ATAGTTAAAAATGATCTGTTCTACAGGGTGAGCAATTCTAATATGTGAGA

GCTGGTAGAACAGTTAATGGCCCCAAGGAAGTATAAAACAACAGTTTTGA

AACTAGCCCATGGTCATTTTTAGAGGGACAATTGGGAGTTCAGAAAACA

AGGGAACACATTTAAAAAGGTTTTATTGGATAGGAATATATCAAGAAGT

GGAACAGTTTTGTGGGGCATGTCCAGAATGCCAATTGGTGTTGGCACAGA

AACTGAGTTGAGCACCTTCAG.
```

The information of the primers for the genome-specific gene sequence fragment of female *Acipenser dabryanus* and the method for identifying the sex of *Acipenser dabryanus* is listed as follows.

| Primer | Sequence information | Annealing temperature (° C.) |
|---|---|---|
| R6R2F (represented by SEQ ID NO: 3) | AGGGAGATTGTTGACTAGGAT | 58 |
| R6R2R (represented by SEQ ID NO: 4) | GACGGTTCTTGGCGACT | 58 |
| R4R3F (represented by SEQ ID NO: 5) | TTGGAGAAGCCTACTGG | 58 |
| R4R3R (represented by SEQ ID NO: 6) | CTGAAGGTGCTCAACTCA | 58 |

The genome-specific primer of female *Acipenser dabryanus* R6R2 is the primer of the nucleotide sequence of SEQ ID NO:1.

The sequence R4R3 is the primer of the nucleotide sequence of SEQ ID NO:2, and the Primer R4R3 is used in conjunction with the primer R6R2.

The primers described in the present invention are used to perform PCR amplification on the DNA of the *Acipenser dabryanus* to be tested. When a resultant product from the amplification shows 3 bands on an agarose gel, the *Acipenser dabryanus* to be tested is female; when a resultant product from the amplification shows 2 bands on an agarose gel, the *Acipenser dabryanus* to be tested is male. Alternatively, when a resultant fragment from the amplification has a 1402 bp band, the *Acipenser dabryanus* to be tested is female, and if there is no 1402 bp band, it is male.

The method for identifying the sex of *Acipenser dabryanus* comprises the following steps: firstly extracting the DNA of the *Acipenser dabryanus* to be tested, then performing PCR amplification on the DNA sample by means of the forementioned primers, next putting a resultant product from the PCR amplification on a 1% agarose gel to perform cataphoresis for 30 min under a voltage of 120V, so as to segregate DNA, finally counting the band sizes of the resultant product from the PCR amplification according to the separation results. The PCR amplification system described in the present invention has a volume of 25 μL consisting of 3 μL of 10×PCR buffer liquid, 2 μL of 2.5 mmol/L dNTP, 3 μL of MgCl$_2$, 1 μL of respective forward and backward primers, 0.5 μL of Taq enzymes, 2 μL of DNA templates, and 10.5 μL of ultrapure water. The PCR amplification described in the present invention comprises: performing predenaturation on DNA at 94° C. for 3 min, performing denaturation on DNA at 94° C. for 30 s, performing renaturation on DNA at an annealing temperature for 30 s and extending primers at 72° C. for 55 s, then repeating the latter three steps 35 times (repeating the steps of performing denaturation on DNA at 94° C. for 30 s, performing renaturation on DNA at an annealing temperature for 30 s and extending primers at 72° C. for 55 s), next extending primers at 72° C. for 10 min and storing at 4° C.

By means of the gene sequence provided by the present invention, we can make an accurate identification whether an *Acipenser dabryanus* fish is a male or a female, which is verified in the examples, and completely consistent with the actual result, and its accuracy is 100%.

Compared with the prior art, the present invention has the following advantages:

The present invention can be used to quickly and accurately identify the sex of *Acipenser dabryanus* and enables hologynic breeding of *Acipenser dabryanus*, which saves breeding space and rationally makes use of the labor, material and financial resources for breeding *Acipenser dabryanus*.

The primer R6R2 according to the present invention has unique properties. Previously disclosed sex-specific markers for any species have the properties that give a reaction product just in females or males, for example, the previously disclosed sex-specific marker for the Chinese sturgeon gives a reaction product just in females, no reaction products in males, therefore, it is called a sex-specific marker of Chinese sturgeon, thus people can judge the information about the male and female to be tested based on this properties. However, when an experimental error during the experimental reaction causes a failure and results in no reaction product, experimenters will mistakenly think that the sample to be tested is male according to the presence or absence of experimental reaction products, thus this results in experimental errors. The primer R6R2F according to the present invention gives two kinds of reaction products in female *Acipenser dabryanus*, and one reaction product in male *Acipenser dabryanus*, avoiding the occurrence of misjudgment of experimental results caused by experimental errors. Therefore, the primer R6R2 according to the present invention is superior to the sex-specific markers for all species that have been currently reported.

The present invention enables hologynic breeding of *Acipenser dabryanus*, which saves breeding space and rationally makes use of the labor, material and financial resources for breeding *Acipenser dabryanus*. This method enables an atraumatic sex identification for *Acipenser dabryanus*.

This method has more advantages than another traditional sex identification method (egg retrieval method) for *Acipenser dabryanus*. The egg retrieval method needs to perform a laparotomy on the *Acipenser dabryanus* over 3 years old and take out a part of its eggs for identification, so this method will cause great damage to *Acipenser dabryanus*. This method avoids experimenters from misreading the experimental results caused by various errors during the experimental manipulation, for instance, even unsuccessful extraction of DNA and error in adding drugs or samples will not cause deviation to the experimental results of this method.

This method avoids experimenters from misreading the experimental results caused by various errors during the experimental manipulation, for instance, even unsuccessful extraction of DNA and error in adding drugs or samples will not cause deviation to the experimental results of this method. If the experiment fails, the positive reference primer according to the present patent can help to quickly determine whether it is caused by a specific primer.

This method can help to raise the populations of the artificially-bred *Acipenser dabryanus*, artificially adjust the ratio of males and females of *Acipenser dabryanus* in breeding, and make more reasonable use of breeding facilities. This method can artificially adjust the ratio of males and females of the *Acipenser dabryanus* released into the wild, and alleviate the sex ratio imbalance of the *Acipenser dabryanus* in the wild so as to promote the natural reproduction of wild *Acipenser dabryanus*, assists in protecting the farmed *Acipenser dabryanus* and the wild *Acipenser dabryanus*, and enhance the working efficiency of biodiversity conservation in natural environment.

DETAILED DESCRIPTION

Figure 1:
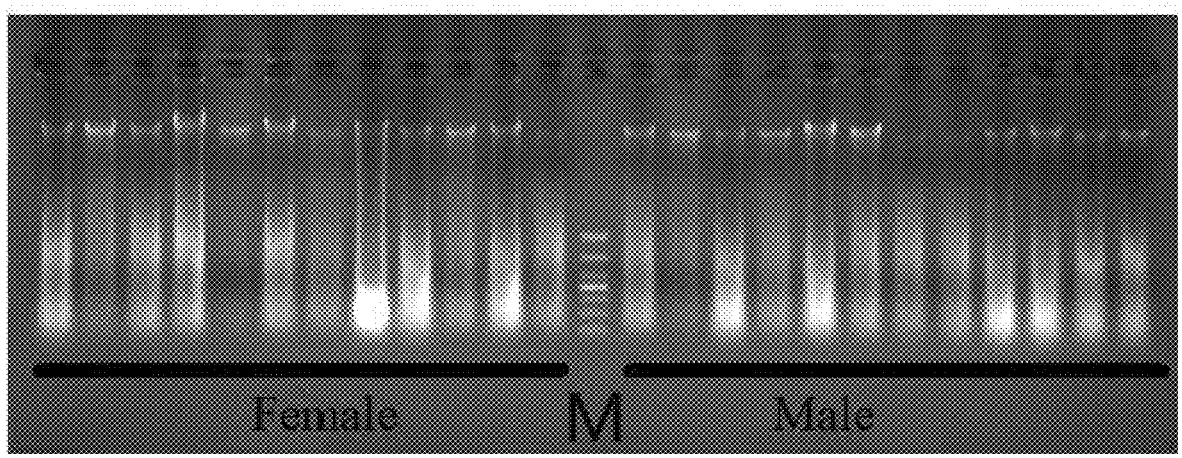
FIG. 1 shows an effect map of the DNA extracted from *Acipenser dabryanus*.

In order to make the objective, technical solution and advantage of the present invention more clear, we shall describe the technical solution of the present invention in detail as follows. Obviously, the examples are only a part of embodiments of the present invention, rather than all embodiments. All other embodiments obtained by a person skilled in the art based on the embodiments in the present invention under the conditions of no creative work should fall within the scope of the present invention.

Example 1

Extracting the DNA of *Acipenser dabryanus* to be Identified:

In April 2021, the applicant trimmed some fins off 12 female *Acipenser dabryanus* that had spawned and off 12 male *Acipenser dabryanus* that had ejaculated, respectively, all derived from the Yichang Experimental Station of the Chinese Sturgeon Research Institute of China Three Gorges Corporation, so as to make samples. The method for extracting the DNA of these 24 *Acipenser dabryanus* is detailed as follows.

(1) Take out the preserved fin sample, then trim about 0.5 g of specimens off it, next put the specimens into a sterilized centrifuge tube of 2 mL, next add 1×TE sterile buffer liquid in the tube, and finally soak the specimens in the sterile buffer liquid at 4° C. for 12 h.

(2) Take out the fin tissue and put it into sterile buffer liquid containing 350 µL of extraction liquid, then mix them lightly, next add 40 µL of 20% SDS and 10 µL of 20 mg/mL proteinase K (its final concentration is 400 µg/mL), finally mix well.

(3) Incubate at 56° C. for 4 h and shake the centrifuge tube lightly every half hour for tissue dissociation. If the tissue is not easily dissociated, incubating may be prolonged to 8 h, or the tissue dissociation may be prolonged at 37° C. overnight.

(4) When the tissue is completely dissociated, take out the centrifuge tube, add 300 µL of 6 M NaCl solution into it, and immediately vibrate it vigorously for 30 s.

(5) Centrifugate the centrifuge tube at 12000 rpm for 10 min.

(6) Trash the deposition, and pour the supernatant into a new centrifuge tube, then centrifugate it again under the same conditions, next take the supernatant and add the pre-cooled isopropanol having the volume equal to it into the new centrifuge tube, finally leave it at 20° C. for more than 1 h.

(7) Centrifugate the new centrifuge tube at 12000 rpm and 4° C. for 15 min.

(8) Trash the supernatant, then wash the deposition once with 700% ethanol solution, next dry up it at 37° C. or air it to give a DNA specimen.

(9) Add the DNA specimen into 50 µL of sterilized double-distilled water to dissolve DNA, and dilute the DNA specimen into 100 ng/µL after complete dissolution, then store the DNA specimen in a refrigerator at 4° C. for later use.

(10) Identify the integrity of the extracted DNA by means of a 1% agarose gel and Marker that is DL1000. The results are shown in FIG. 1, which shows that the DNA of these 24 *Acipenser dabryanus* is completely successfully extracted.

Example 2

Figure 2:
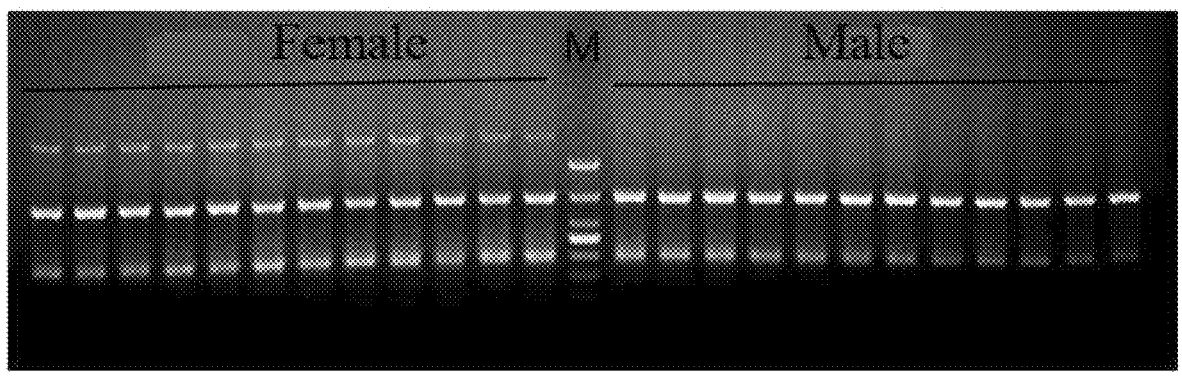
FIG. 2 shows a sex identifying map of *Acipenser dabryanus*.

Identifying the Sex of *Acipenser dabryanus*:

The inventors use the primers provided by the present invention to perform PCR reaction on the DNA of 24 *Acipenser dabryanus* from Example 1 (12 males and 12 females are sampled). The PCR amplification system has a volume of 25 µL consisting of 3 µL of 10×PCR buffer liquid, 2 µL of 2.5 mmol/L dNTP, 3 µL of MgCl$_2$, 1 µL of respective forward and backward primers, 0.5 µL of Taq enzymes, 2 µL of DNA templates, and 10.5 µL of ultrapure water. The PCR reaction comprises: performing predenaturation on DNA for 3 min, performing denaturation on DNA at 94° C. for 30 s, performing renaturation on DNA at an annealing temperature for 30 s and extending primers at 72° C. for 55 s, then repeating the latter three steps times, next extending primers at 72° C. for 10 min and storing at 4° C., next putting a resultant product from the PCR amplification on a 1% agarose gel to perform cataphoresis for 30 min under a voltage of 100V. The result can be observed on a gel illuminator, the detailed results are shown in FIG. 2. It can be seen from FIG. 2 that the 12 female *Acipenser dabryanus* identified by the egg retrieval method all have three bands, indicating that the 12 female *Acipenser dabryanus* identified by this method are also a female resultantly. The 12 male *Acipenser dabryanus* identified by the egg retrieval method have two bands, indicating that the 12 male *Acipenser dabryanus* identified by this method are also a male resultantly. Of the 24 *Acipenser dabryanus* identified by this method, 12 fish are a male and 12 fish are a female. The result is consistent with that of the record in sampling. This experiment proves the accuracy of this method for identifying the sex of *Acipenser dabryanus*, so this method can be applied to the sex identification for *Acipenser dabryanus*.

The examples described above are only a preferred embodiment of the present invention, but no limitation therefrom is imposed on the patent scope of the invention. Any modification or equivalent substitution made by a person skilled in the art based on the technical solution and the inventive concept within the technical scope disclose by the present invention shall fall within the patent protection scope of the present invention.

SEQUENCE LISTING

```
Sequence total quantity: 6
SEQ ID NO: 1                 moltype = DNA   length = 1402
FEATURE                      Location/Qualifiers
source                       1..1402
                             mol_type = other DNA
                             organism = synthetic construct
SEQUENCE: 1
agggagattg ttgactagga ttcattcgct ctctgtcaca gtcccgcata tgtgatcaag   60
gttcgtagaa cagcttttac ttctgccccct ttgtgctgaa taatttggtg gacattgatg  120
```

SEQUENCE LISTING

```
Sequence total quantity: 6
SEQ ID NO: 1                 moltype = DNA   length = 1402
FEATURE                      Location/Qualifiers
source                       1..1402
                             mol_type = other DNA
                             organism = synthetic construct
SEQUENCE: 1
agggagattg ttgactagga ttcattcgct ctctgtcaca gtcccgcata tgtgatcaag     60
gttcgtagaa cagcttttac ttctgccccct ttgtgctgaa taatttggtg gacattgatg   120
tagtgagtcc atttcctggg aatgaatagc aaacccagtg tgttattggc ccttgtccca   180
atagtgtgat ccatcaatat acactgatgt ggcagtgaca tcgggtgtgg ttgtaaaggg   240
agacggcaga tgtgtttgtg ggggggggtgc agtcatgtgg ggtaccgtgg tatagcaggg   300
ctgtgggaag catggcaact ggtatgtgtt tacatgacag gtttcgttct gataaagaca   360
gggtccaccc ggccaatcga gcgttggata tgcccttaac gctgccattg agcaaaagtt   420
ggataggagt gtgttctgtt tgcactgtaa tgtgttgaaa acctgtaata aatttgaaat   480
atagaacagc ccaatataca gatagcaggt gacgagtaca ctgatcaaaa gcttgctcaa   540
cggctttgag tagccttgaa gcgtaggcga cgggatgtag cttggtatttt acttcctgta   600
acaaactgc  agagagaagt tttggtagct gcagtctgca aaataagggg ttcattagaa   660
gccagatttc ggagggcatg tgcttctagc agggaggctt tgagagattc aaaagcagtc   720
taatgtttgc tttcccatac caacacatcc ttgcctttcc tggaaccttt caacagatca   780
taaagtggtt tagccttgga tgaaaagtcc tcaaactcac aacaaaaatt gaccagacct   840
agaaaggaac gtaaagcagt tttcagaggt tggcacaggc agccactgta cagttttcca c  900
tttgtgtttg tctggggacc gtcctccttc ctcaatgagt accccctagaa aagtaacaga   960
aggttgcatt agttgtgctt ttttgggttc agattgagtc ctgcattctc tgttgttgtc  1020
aacagctcat ccagcagtga gagatgctcc tcctttgagt gtctgtcagt aagtcatcga  1080
cataatgtat taaacattgg ggtttagaga agcaggacaa aatttcagaa agtatttggt  1140
gaaagagcgt gggagagttg tggaacccctt gcggaatttt attccaggta tactgtgtat  1200
cgccaaaagt gaaaccaaat ttatagcgtg attctggttt cactggcaga gaccagaaac  1260
cattaaaaat gtcaagagcg gtgtaatagc aggcagaagg ggttaactca gaaagcacat  1320
ttgggggtaga tgcgtctaca ggtgcgcata taggtgtgtg tttaagttcc atgtaatcaa  1380
ttgtaagtcg ccaagaaccg tc                                           1402

SEQ ID NO: 2                 moltype = DNA   length = 321
FEATURE                      Location/Qualifiers
source                       1..321
                             mol_type = other DNA
                             organism = synthetic construct
SEQUENCE: 2
ttggagaagc ctactgggaa agacgcagaa atttttaattt cccaaatgtt atagttaaaa    60
atgatctgtt ctacagggtg agcaattcta atatgtagaa cagttaatgg                120
ccccaaggaa gtataaaaca acagtttttga aactagccca tggtcatttt ttagagggac   180
aattgggagt tcagaaaaca agggaacaca tttaaaaaag gttttattgg ataggaatat   240
atcaagaagt ggaacagttt tgtggggcat gtccagaatg ccaattggtg ttggcacaga   300
aactgagttg agcaccttca g                                             321

SEQ ID NO: 3                 moltype = DNA   length = 21
FEATURE                      Location/Qualifiers
source                       1..21
                             mol_type = other DNA
                             organism = synthetic construct
SEQUENCE: 3
agggagattg ttgactagga t                                              21

SEQ ID NO: 4                 moltype = DNA   length = 17
FEATURE                      Location/Qualifiers
source                       1..17
                             mol_type = other DNA
                             organism = synthetic construct
SEQUENCE: 4
gacggttctt ggcgact                                                   17

SEQ ID NO: 5                 moltype = DNA   length = 17
FEATURE                      Location/Qualifiers
source                       1..17
                             mol_type = other DNA
                             organism = synthetic construct
SEQUENCE: 5
ttggagaagc ctactgg                                                   17

SEQ ID NO: 6                 moltype = DNA   length = 18
FEATURE                      Location/Qualifiers
source                       1..18
                             mol_type = other DNA
                             organism = synthetic construct
SEQUENCE: 6
ctgaaggtgc tcaactca                                                  18
```

What is claimed is:

1. A method for identifying a sex of *Acipenser dabryanus*, comprising the following steps:

performing PCR amplification on the DNA of the *Acipenser dabryanus* to be tested, and judging that the *Acipenser dabryanus* to be tested is female when a resultant product from the amplification shows 3 bands on an agarose gel and the *Acipenser dabryanus* to be tested is male when a resultant product from the amplification shows 2 bands on an agarose gel, alternatively, judging that the *Acipenser dabryanus* to be tested is female when a resultant fragment from the amplification has a 1402 bp band and it is male if there is no 1402 bp band, wherein the method uses a difference in a number of the bands of PCR products, and comprises the following steps:

extracting the DNA of the *Acipenser dabryanus* to be tested, performing PCR amplification on the DNA sample by primers which comprises a sequence with SEQ ID NO: 3; a sequence with SEQ ID NO: 4; a sequence with SEQ ID NO: 5; and a sequence with SEQ ID NO: 6, putting a resultant product from the PCR amplification on a 1% agarose gel to perform cataphoresis for 30 mins under a voltage of 120 V, so as to segregate DNA, and counting band sizes of the resultant product from the PCR amplification according to segregated results.

2. The method for identifying a sex of *Acipenser dabryanus* according to claim 1, wherein a system of the PCR amplification has a volume of 25 µL consisting of 3 µL of 10×PCR buffer liquid, 2 µL of 2.5 mmol/L dNTP, 3 µL of $MgCl_2$, 1 µL of respective forward and backward primers, 0.5 µL of Taq enzymes, 2 µL of DNA templates, and 10.5 µL of ultrapure water.

3. The method for identifying a sex of *Acipenser dabryanus* according to claim 1, wherein the PCR amplification comprises the following steps:

performing predenaturation on DNA at 94° C. for 3 mins, performing denaturation on DNA at 94° C. for 30 s, performing renaturation on DNA at an annealing temperature for 30 s and extending primers at 72° C. for 55 s, then repeating the denaturation, renaturation and extending steps 35 times, extending primers at 72° C. for 10 mins, and storing at 4° C.

* * * * *